Figure 1:
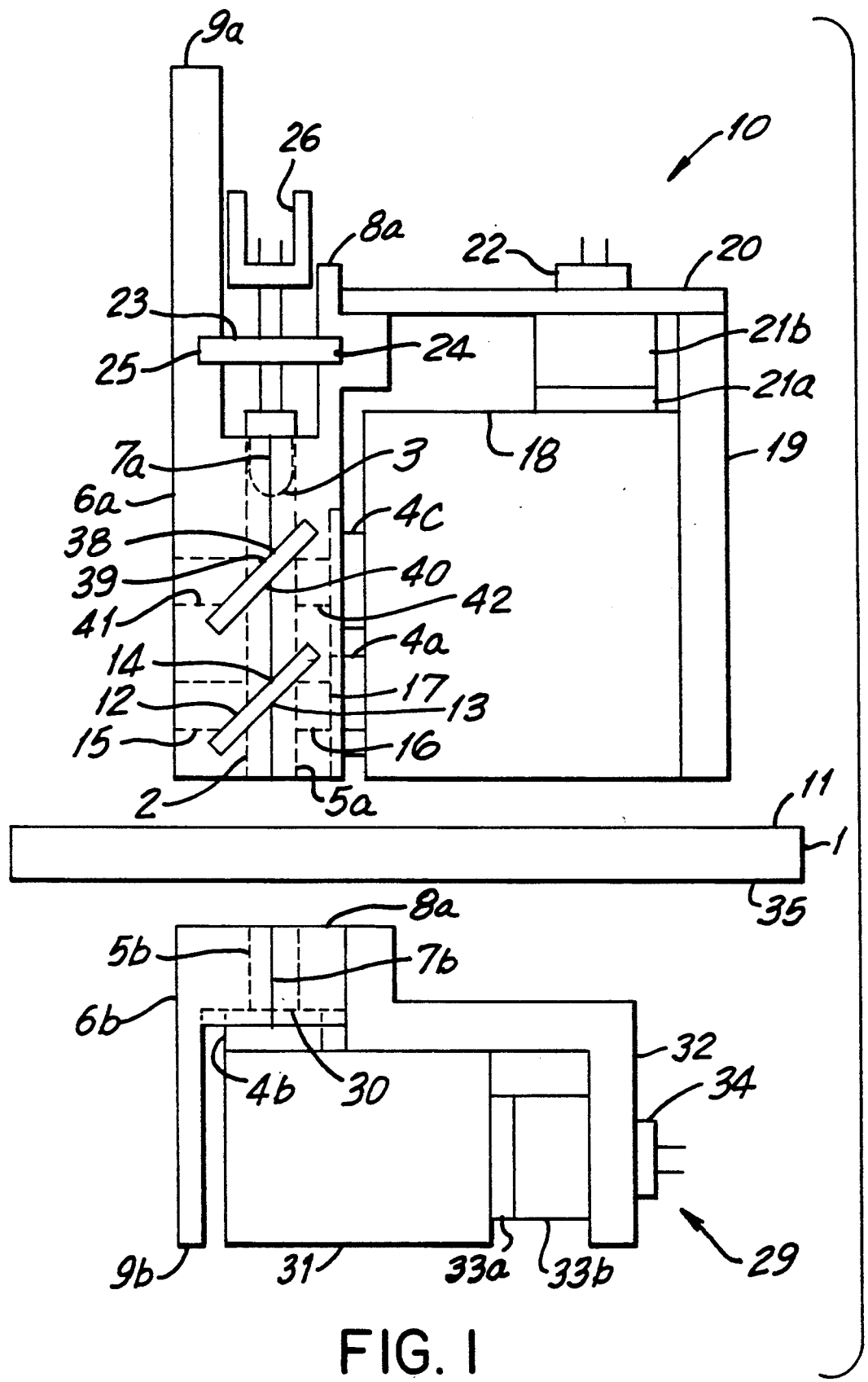

United States Patent [19]
Schoeps

[11] Patent Number: 5,268,747
[45] Date of Patent: Dec. 7, 1993

[54] APPARATUS FOR THE SIMULTANEOUS NON-CONTACTING TESTING OF A PLURALITY OF POINTS ON A TEST MATERIAL, AS WELL AS THE USE THEREOF

[75] Inventor: Wilfried Schoeps, Koblenz, Switzerland

[73] Assignee: Schwizerische Eidgenossenschaft Paul Scherrer Institute, Villigen, Switzerland

[21] Appl. No.: 490,640

[22] PCT Filed: Oct. 30, 1989

[86] PCT No.: PCT/CH89/00187

§ 371 Date: Aug. 30, 1990

§ 102(e) Date: Aug. 30, 1990

[87] PCT Pub. No.: WO90/05297

PCT Pub. Date: May 17, 1990

[30] Foreign Application Priority Data

Oct. 30, 1988 [CH] Switzerland ............... 4054/88
Oct. 30, 1988 [CH] Switzerland ............... 4055/88

[51] Int. Cl.⁵ .................................. G01N 21/55
[52] U.S. Cl. .................... 356/445; 356/432; 356/429; 356/430; 356/431
[58] Field of Search ............ 356/445, 432, 432 T, 356/440, 378, 380, 381, 382, 355, 356, 357, 360, 416, 417, 414, 419, 429, 430, 431

[56] References Cited

U.S. PATENT DOCUMENTS 4,722,607 2/1988 Anselment et al. ............... 356/417
4,854,710 8/1989 Opsal et al. ............... 356/445
4,910,402 3/1990 McMillan ............... 356/445

Primary Examiner—Vincent P. McGraw
Assistant Examiner—La Charles P. Keesee
Attorney, Agent, or Firm—Egli International

[57] ABSTRACT

The apparatus comprises at least one light source (3) and a plurality of test channels with in each case one optoelectronic converter (4a, 4b). In the light path between the light source and the converter is provided at least one light channel (5a, 5b) and the test material (1). The light channels are constructed as optical elements for bounding or defining a light bundle. A plurality of light channels is juxtaposed in a common casing (6a, 6b) on at least part of the light path. In each light channel can be provided a beam splitter element (12) and together form a single beam splitter (12) removably arranged in the casing. The converters (4a) can be juxtaposed on the same casing as the beam splitter (12) and each is associated with a light channel (5a). Two casings (6a, 6b) can be provided, the light source (3) in the first casing (6a) and the converters (4b) in the second casing (6b) are juxtaposed and associated with in each case one light channel (5a, 5b). At least one part (5b) of each light channel can be arranged in the second casing (6b). The light channels (5a, 5b) can have a common plane of symmetry (7a, 7b) and a casing (6a, 6b) can be constructed in two parts with parts (8a, 9a; 8b, 9b) separable from one another in the plane of symmetry. The light sources (3) and converters (4a, 4b) can be positioned remotely of casing (6a, 6b) and can be connected to the light channels (5a) via light guides.

21 Claims, 7 Drawing Sheets

APPARATUS FOR THE SIMULTANEOUS NON-CONTACTING TESTING OF A PLURALITY OF POINTS ON A TEST MATERIAL, AS WELL AS THE USE THEREOF

The invention relates to an apparatus for the simultaneous non-contacting testing of a surface or internal interface of a test material by means of incident light or a layer or spatial portion of the test material by means of back-scattered or back-reflected transmitted light, in which the apparatus comprises at least one light source and a plurality of test channels, each test channel comprising an optoelectronic converter and at least one light channel arranged in the light path between the light source and the converter and in which is positioned a beam splitter element, each light channel is constructed as an optical element for defining a light bundle, on at least part of the light path located within the same the light channels are juxtaposed in a common casing and constructed as recesses passing through said casing and the test material is arranged in the light path between the light source and the converter.

The invention also relates to the use of this apparatus for testing a supposedly smooth or regularly structured surface for irregularities thereof, or for testing a light transmitting, supposedly homogeneous or regularly structured layer for irregularities or inhomogeneities thereof and inclusions, or for testing a supposedly stationary surface or internal interface of the test material for position changes to said surface, or for testing a light transmitting, supposedly stationary spatial portion of the test material for movements and in particular vibrations of inhomogeneities or inclusions in the test material, as well as particles floating or suspended in the latter, or for testing the concentricity of a shaft for concentricity errors, particularly vibrations.

These are uses which are in part the same as in the laser scanner inspection systems (LSIS). The latter require a mechanically operated scanning system, such as e.g. a rotating mirror polygon, as well as a light collecting device, such as e.g. a light guide for guiding the scanning light beam to an optoelectronic converter. They are therefore expensive, bulky and susceptible to faults, particularly due to wear, because they do not operate in a static manner. They also do not permit the uninterrupted or continuous testing of a face moving past in a relative movement or a surface of a rotating shaft moving past in a relative movement. The combination of the moving past of the test material in the longitudinal direction and the scanning of the latter in the transverse direction, or the combination of the rotation and scanning of the test material gives on the latter a zig-zag tested surface, which limits the maximum speed with which it can pass under the LSIS if its entire surface is to be uninterruptedly tested and such as is necessary when testing the concentricity of a shaft. Thus, standard textile webs with a width of 4 m in the case of the presently standard passage speeds of 600 m/min and standard rotational speeds of rapidly rotating shafts of approximately 10 m/s are too fast to be tested continuously with LSIS. Moreover, if not only the concentricity of the shaft, but also its rapidly superimposed vibrations are to be tested, such a test or inspection is not possible with LSIS.

WO-87/3957 discloses an elementary optoelectronic testing device, which comprises a light source and a test channel with an optoelectronic converter and a light channel arranged in the light path between the light source and the converter. The test material is arranged in the light path between the light source and the converter. The light channel has a wall which supports a half-mirror and the converter and therefore has a certain thickness in order to give the necessary strength. A certain amount of space is also required by the holders for the half-mirror and the converter on the light channel.

It is admittedly obvious to attempt to assemble an apparatus of the aforementioned type from those elementary testing devices according to WO-87/03957, by juxtaposing the same. However, this is not possible, because the testing devices according to WO/87-03957 cannot be sufficiently closely juxtaposed in order to continuously test a test material moving past (relative movement, vibration, rotation). Even if the testing devices are arranged in one or two staggered rows, the wall thickness and holders will take up too much space to permit the desired packing density of the light channels and consequently the testing devices. The desired result would only be attainable with more than two displaced rows, which would involve correspondingly increased costs.

A testing device of the same type is also known from FR-2491615. Testing devices known e.g. from DE-3428435, GB-2025041, U.S. Pat. No. 3,736,065 and LU-56099 operate according to the same principle. However, none of the aforementioned documents makes any reference to the solution of the aforementioned packing density problem. A testing device known from SU-666418 has a row of photodiodes in a casing, but provides no information as to how one or more rows of elementary testing devices can be housed with a high packing density in a casing.

The problem of the present invention is to provide an apparatus of the aforementioned type with which it is possible to achieve such a packing density of juxtaposed testing devices that a continuous or uninterrupted testing or inspection of the test or inspection material is attainable. In the case of a test material moving past (relative movement, vibration, rotation), it must be possible to achieve uninterrupted testing with a maximum of two rows of testing devices. For the uninterrupted testing of stationary, flat test material or a supposedly stationary surface or an internal interface, or a light transmitting, supposedly stationary spatial portion of the test material, or for the uninterrupted testing of the concentricity of a shaft, several rows of testing devices, which are optionally reciprocally staggered, must be juxtaposable with the necessary packing density. This problem is solved in that the light channels have a common plane of symmetry, the casing is constructed in two parts with parts separable from one another in the plane of symmetry, the beam splitter elements are constructed as parts of a beam splitter forming a single subassembly and removably arranged in the casing, and the converters are arranged on the same casing as the beam splitters in juxtaposed manner and in each case corresponding to a light channel.

Preferably the test material-side ends of the light channels are congruent with a surface which is constructed and arranged parallel to a surface of the test material. The light sources are preferably formed by light emitting diodes or laser diodes corresponding in each case to one light channel, which are positioned remote from the casing and connected via light guides to the light channels. The converters are preferably formed by photodiodes corresponding in each case to one light channel, which are positioned remote from the casing and are connected to the light channels via light guides, which in turn can be at least partly arranged in at least part of a light channel. The two parts of the casing are preferably provided with corresponding recesses which, on joining together the parts, form a recess for receiving the individual subassembly of the beam splitter. The light channels can contain polarization and/or colour filter elements, which are constructed as parts of a polarization and/or colour filter removably arranged in the casing and forming a single subassembly and the two parts of the casing can be provided with corresponding recesses, which on joining together the parts together form a recess for receiving the individual subassembly of the filter. The beam splitter elements are preferably constructed as strip mirror elements and then in each light channel can be arranged a second strip mirror element, whose strips are semitransmitting and substantially correspond to the strips of the beam splitter element constructed as a strip mirror element. The strip mirror elements are constructed as parts of a semitransmitting strip mirror forming a single subassembly and removably arranged in the casing. Preferably each light channel contains a second beam splitter element. The second beam splitter elements are constructed as parts of a second beam splitter forming an individual subassembly and removably arranged in the casing. In each case a second converter is positioned opposite to the second beam splitter element in the same way as the first converter is positioned facing the first beam splitter element.

As a result of the inventive arrangement of the light channels in juxtaposed manner in a common casing, the packing density of the juxtaposed testing devices can be increased to such an extent that it is possible to attain an uninterrupted testing or inspection of the test material moving past (relative movement, vibration, rotation) with a maximum of two rows of light channels. As a function of the collimation achieved in the light channels, it is even possible to achieve an uninterrupted testing of the test material with a single row of light channels. Thus, the inventive apparatus is static, small, robust and inexpensive to manufacture, so that it can be used in place of LSIS.

Through replacing LSIS by the inventive apparatus, in the case of uninterruped testing of the test material, its passage speed (relative movement, vibration, rotation) can be significantly increased compared with what has been hitherto achievable, because the achievable limit for the passage, vibration or rotational speed of the test material is now only determined by the optoelectronic signal processing and the passage speed can e.g. be 1000 m/min and the vibrational or rotational speed can e.g. be more than 10 m/s. Unlike in the case of LSIS, the length of the row of light channels is unlimited in the inventive apparatus, so that in the case of the latter there is also no restriction to the size of the test material moving past and it can e.g. have a width of 10 m. Even in the case of such a wide and rapidly passing or large and rapidly vibrating or rotating test material, the nominal detection range of 10 to 500 $\mu$m resulting from the measuring principle in the case of a spatial error resolution of 2.5 mm is still attainable and it is possible to detect 5 $\mu$m holes.

In the case of constructing the inventive apparatus with a plurality of light sources, which in each case correspond to a light channel and which are formed from light emitting diodes or laser diodes, if a light source fails, only one channel and not the complete apparatus fails, so that during the breakdown only a very small part of the test material remains untested.

Due to the small dimensions of the apparatus according to the invention, it can be housed in casings under restricted spatial conditions, e.g. in vacuum bells of vapour deposition systems, spraying systems and the like, which is not possible with LSIS due to the dimensions of such systems. Due to the small dimensions of the inventive apparatus, it can also be housed within pipes and sections, which is not possible with LSIS due to the dimensions of such systems.

Under these circumstances and due to these advantages, the inventive apparatus can be used for testing a supposedly stationary surface or internal interface of the test material for positional changes thereof, which are e.g. caused by movement, vibration, expansion, shrinkage, growth, deposits, etc., or for testing the concentricity of a shaft for concentricity errors, particularly vibrations, optionally as a function of the rotational speed of the shaft, or for testing a light transmitting, supposedly stationary layer or a light transmitting, supposedly stationary spatial portion of the test material for movements and in particular vibrations of inhomogeneities or inclusions in the test material, as well as particles suspended or floating in the test material.

Examples of such uses are compact disks and glass products such as mirrors, disks and pipes, in the semifinished or finished state. Thus, it has not hitherto been appropriate for price reasons to test compact disks both before and after coating the blank, so that it was necessary to make do with testing following coating. The inventive apparatus makes it possible to carry out both tests and reduce costs. Other examples relate to tests on the behaviour of mechanical parts such as aircraft wings, or the advance of physical processes, such as expansion, shrinkage, condensation, precipitation, evaporation, phase changes, crystallization, polarization changes of areas, slow chemical reactions, such as corrosion or rapid chemical reactions, such as explosions, biological processes such as the growth of microbiological cultures, plants, etc. or tests on stationary or flowing gases or liquids, emulsions, suspensions, etc., e.g. with respect to chemical effects, such as colour, polarization or density changes, hydrodynamic or acoustic effects, formation of vapour bubbles, flow rates, content of entrained particles or bubbles, etc.

It is stressed that accelerometers and resistance strain gauges of the conventional type require connecting wires, whereas the inventive apparatus operates in noncontacting manner.

According to a variant of the use, it is possible to use on one side of the test material an apparatus for testing by means of incident light or back-scattered transmitted light and on the other side of the test material a retroreflector for the transmitted light. In another use variant it is possible to provide on one side of the test material an apparatus for testing by means of incident light or back-scattered transmitted light and on the other side thereof an absorber for the transmitted light.

Thus, the apparatus according to the invention can test in different ways different types of irregularities, inhamogeneities, inclusions and movements and supply correspondingly differentiated results enabling conclusions to be drawn regarding their causes.

Among the uses of the apparatus according to the invention over and beyond those already mentioned, reference is e.g. made to the testing of uncoated or metal-coated or colour-coated polymer foils and films, metallic or metal-coated objects such as compact disks, uncoated, coated or coloured paper in web or sheet form, uncoated or metal-coated or colour-coated flat glass, uncoated or coated textile articles on surfaces or coating defects such as irregularities, deposits, scratches, dust particles, holes, cavities, inclusions, colour or optical differences, rough points, grooves, etc., as well as structural variations regarding the crosslinking or pattern or printing quality.

In an exemplified construction of an inventive apparatus intended for testing passing webs with a width of 250 mm, in both casings there are 96 light channels with a cross-section of 2.54×2.54 mm in two staggered rows of in each case 48 light channels.

In another exemplified construction of an inventive apparatus used for testing compact disks with a diameter of 130 mm at a rate of max 8 seconds per plate, in one or two casings are provided 32 light channels with a cross-section of 2.54×2.54 mm in two staggered rows of in each case 16 light channels. In both cases, fully reflecting surfaces can be tested in the reflection mode.

For testing partly reflecting surfaces of transparent test material, it is possible to place a black light absorber under the same. For testing the interior of transparent or light-transmitting test material a mirror can be placed under the same and when using a half-mirror the partly reflecting surfaces and the interior can be simultaneously tested.

In another exemplified construction of an inventive apparatus intended for testing the concentricity of a shaft with a length of 250 mm, the two casings contain 96 light channels with a cross-section of 2.54×2.54 mm in two staggered rows of in each case 48 light channels. In the case of a mirror-smooth surface, testing can take place in the reflection mode.

In another exemplified construction of an inventive apparatus used for testing a transparent liquid or gas in a pipe with an inspection glass with a width of 100 mm, in one or two casings are provided 40 light channels with a cross-section of 2.54×2.54 mm in two staggered rows of in each case 20 light channels. For this purpose testing can be carried out in the transmitted light mode with a light source-side casing and a second converter-side casing or on one side in the incident light mode with a facing mirror.

The invention is described in greater detail hereinafter relative to non-limitative embodiments and with reference to the attached drawings, wherein show:

FIG. 1 A diagrammatic side view of a construction of an inventive apparatus with a light source-side, two-part casing and a second, two-part casing in each case for 6 light channels.

Figure 2:
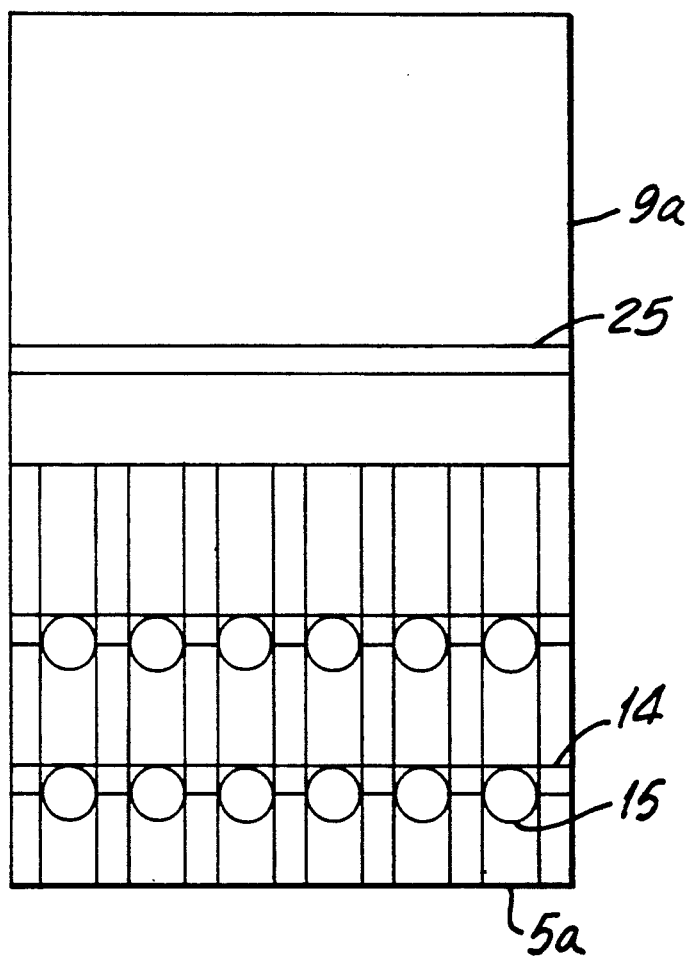

FIG. 2 A diagrammatic front view of the light source-side casing part of the apparatus to the left in FIG. 1.

Figure 3:
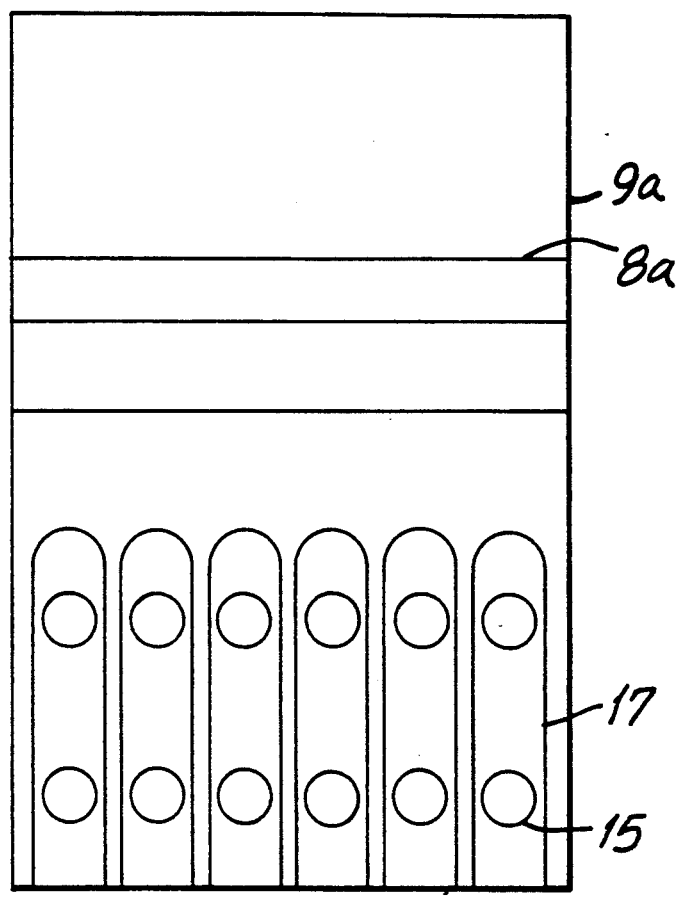

FIG. 3 A diagrammatic rear view of the light source-side casing of the apparatus of FIG. 1.

Figure 4:
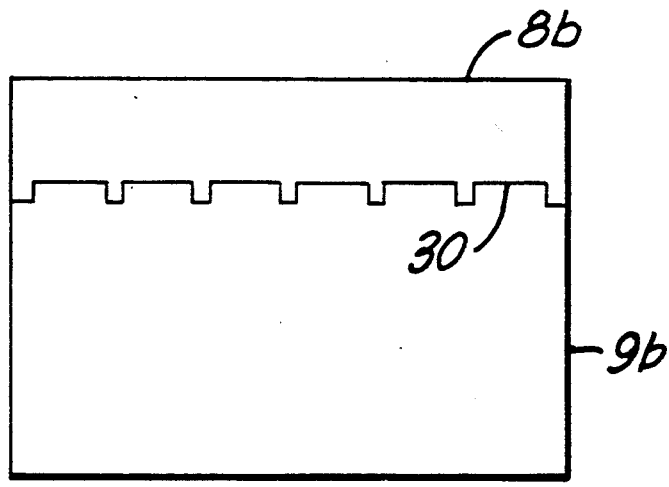

FIG. 4 A diagrammatic rear view of the second casing of the apparatus of FIG. 1.

Figure 5:
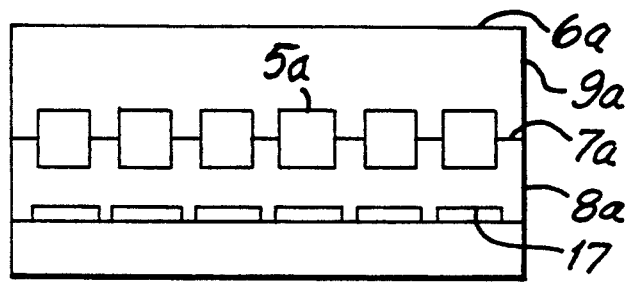

FIG. 5 A diagrammatic view from below of the light source-side casing of the apparatus of FIG. 1.

Figure 6:
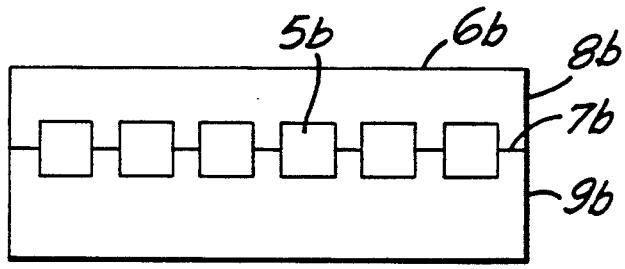

FIG. 6 A diagrammatic plan view of the second casing of the apparatus of FIG. 1.

Figure 7:
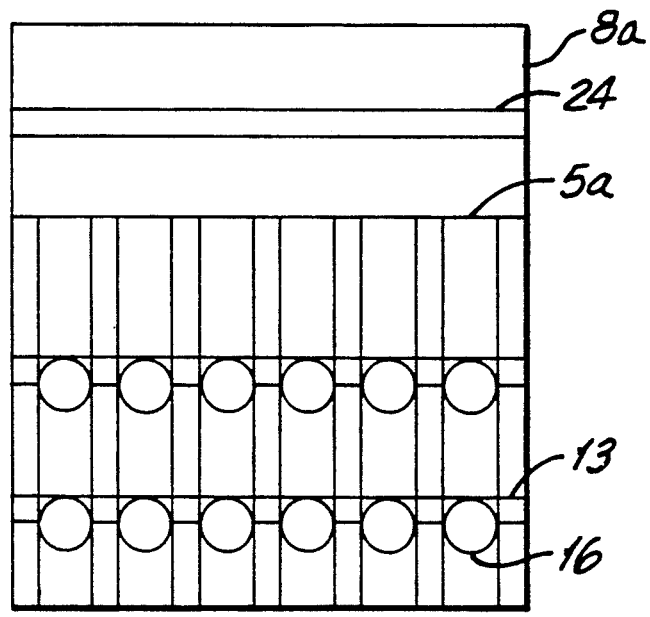

FIG. 7 A diagrammatic rear view of the casing part shown to the left in FIG. 1 of the light source-side casing of the apparatus thereof.

Figure 8:
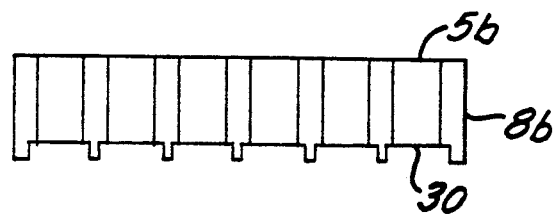

FIG. 8 A diagrammatic front view of the casing part of the second casing shown to the right in FIG. 1.

Figure 9:
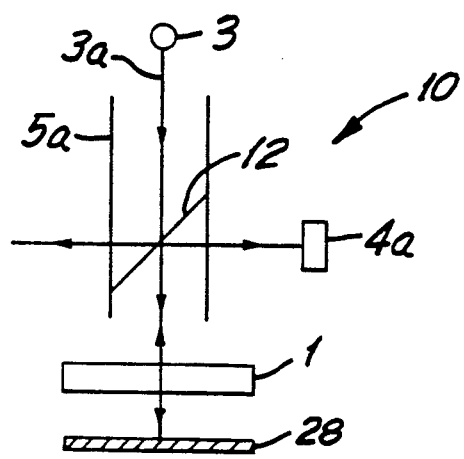

FIG. 9 A diagrammatic view of the optically essential elements of an inventive apparatus in a use for testing a surface or an internal interface of the test material by means of incident light, or a layer or a spatial portion of the test material by means of back-scattered transmitted light.

Figure 10:
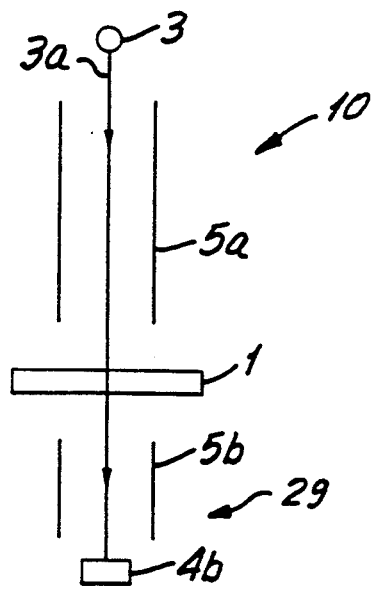

FIG. 10 A diagrammatic view of the optically essential elements of an inventive apparatus in a use for testing a layer or a spatial portion of the test material by means of transmitted light.

Figure 11:
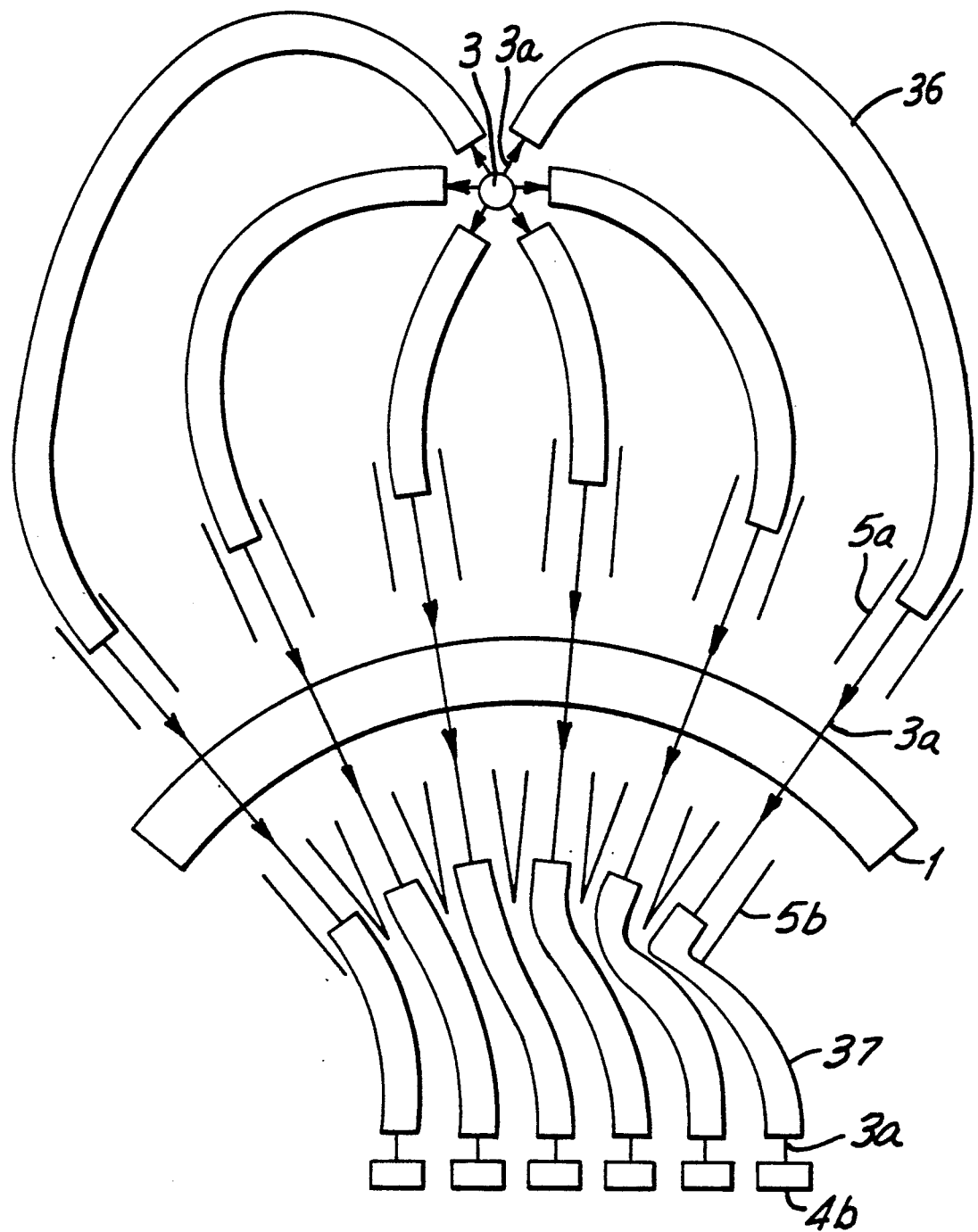

FIG. 11 A diagrammatic view of the optically essential elements of an apparatus based on that of FIG. 1 for testing a curved test material, in which light guides and a single light source are used.

Figure 12:
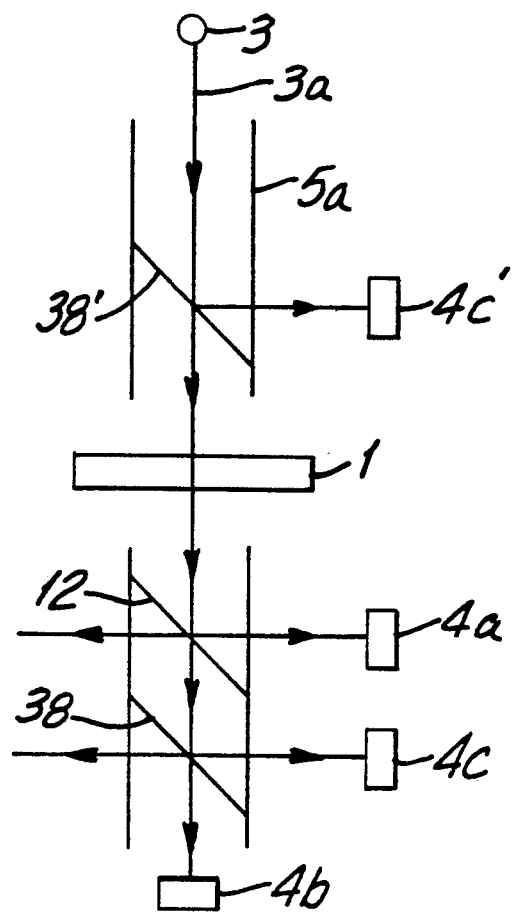

FIG. 12 A diagrammatic view of the optically essential elements of an apparatus derived from that of FIG. 1 for testing a curved test material, in which certain optical elements have been moved into the second casing.

Figure 13:
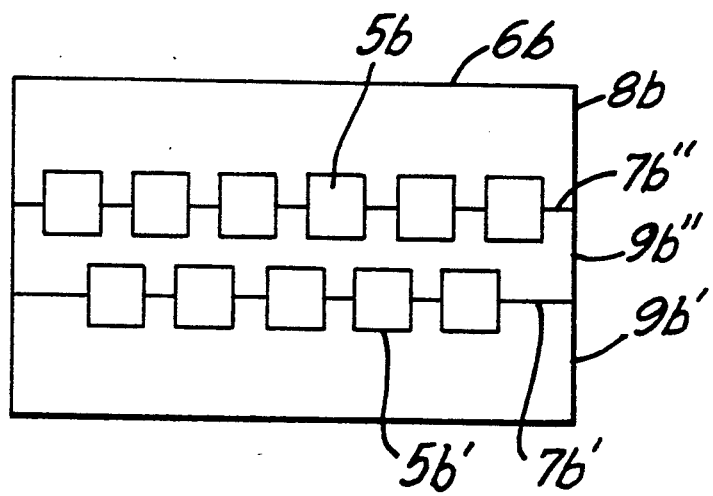

FIG. 13 A diagrammatic plan view of the second casing of the apparatus of FIG. 1 in the case of a construction with two reciprocally displaced rows of test channels.

FIG. 1 shows an embodiment of an inventive apparatus in a diagrammatic side view. This apparatus is intended for the simultaneous non-contacting testing of points of a surface or spatial portion of a test material 1 and functions according to the same principle as the apparatus known from WO-87/03957 and consequently reference should be made to the latter for further details.

The apparatus comprises six test channels 2 with which are associated in each case one light source 3, which is constructed as a light emitting diode, and three optoelectronic converters 4a, 4b and 4c. In the light path between the light source 3 and the converters 4a and 4c a light channel 5a is arranged in each test channel. In the light path between light source 3 and converter 4b is provided a two-part light channel 5a, 5b.

The test material is positioned in the light path between light source 3 and converter 4a, 4b or 4c. Strictly speaking the light channel 5a between light source 3 and converter 4a is also in a two-part form, because the light firstly passes through it from light source 3 to test material 1 and then over part of its length again from test material 1 to converter 4b.

The function of light channel 5a, 5b is to limit the light bundle of the light passing from light source 3 to test material 1, i.e. to keep the divergence between individual light beams of the light bundle smaller than a predetermined angle. In this sense light channel 5a, 5b is an optical element.

In the represented construction this optical element is constructed as a parallelepipedic cavity, which is provided in casing 6a, 6b and in the represented construction six such cavities are juxtaposed in in each case one common first casing 6a or second casing 6b.

As shown, casing 6a, 6b can be constructed in two-part form, in order to facilitate the manufacture of the light channels 5a, 5b, e.g. by milling. This two-part form of the casing is visible in FIGS. 5 and 6, FIG. 5 being a diagrammatic view from below of the light source-side casing 6a and FIG. 6 a diagrammatic plan view of the second casing 6b. FIGS. 1 and 5 show the interface 7a between the two casing parts 8a, 9a of casing 6a, whilst FIGS. 1 and 6 show the interface 7b between the two casing parts 8b, 9b of casing 6b. FIGS. 5 and 6 show the construction of the light channels 5a, 5b on the quadrangular cross-section of the parallelepipedic cavities 5a, 5b, whereof six are juxtaposed and identical to one another, so that when describing the test channels hereinafter (i.e. everything linked with an individual light channel), only one of these need be described. The indicated interface 7a or 7b advantageously forms a plane of symmetry of the particular light channel 5a, 5b.

Above the test material 1, FIG. 1 shows a construction 10 of the inventive apparatus used for testing the upper surface 11 of test material 1 by means of incident light or the complete layer thickness, or the complete thickness of the spatial portion of the test material 1 by means of back-scattered transmitted light. The parallelepipedic cavity 5a passes through casing 6a. The light emitting diode 3 is inserted therein at its end. At its other end, it terminates with the opening 5a visible in FIG. 5 facing the surface 11 of test material 1.

A beam splitter element 12 constructed as a half-mirror is arranged at an angle of 45° to the longitudinal axis of cavity 5a therein, in order to deflect the light reflected or back-scattered by test material 1 to the optoelectronic converter 4a. The beam splitter element 12 is constructed as a semireflecting glass plate, which extends in one piece, i.e. as a single subassembly over the six light channels 5a and the entire width of casing 6a. This glass plate 12 is inserted in corresponding slots 13 or 14 of casing part 8a or 9a, the slots 13 and 14 together forming a recess for receiving the glass plate 12 when casing parts 8a and 9a are joined together. The slot 13 in casing part 8a is more particularly visible in FIG. 7, as well as the half of cavity 5a located in casing part 8a. The slot 14 in casing part 9a is more particularly visible in FIG. 2, as well as the half of cavity 5a located in casing part 9a.

It is clear that the aforementioned dividing into two of the casing 6a into parts 8a, 9a facilitates significantly the manufacture of slots 13, 14 and that, if necessary, the glass plate 12 can be removed from casing 6a by sliding out of slots 13, 14.

A light passage 15 for each test channel is provided in casing part 9a (FIGS. 1 and 2) and leads from cavity 5a to the outside. The light passage 15 enables the light of light emitting diode deflected by glass plate 12 to pass to the outside and is not scattered back by the wall of cavity 5a to the glass plate. For example, the undesired light of light emitting diode 3 deflected by the glass plate 12 can pass through the light passage 15 to a light absorber. It would also be possible to construct the wall of cavity 5a in light-absorbing manner, so that no undesired light of light emitting diode 3 deflected by glass plate 12 returns to the latter and through the latter to photodiode 4a.

Casing part 8a has a light passage 16 for each test channel (FIGS. 1 and 7), which leads from the cavity 5a to the optoelectronic converter 4a. The light passage 16 permits the light coming from the test material and deflected by the glass plate to reach the optoelectronic converter 4a. The latter is an approximately quadrangular photodiode, whose photosensitive side is countersunk in a slot 17 provided for this purpose in casing part 8a (FIGS. 1, 3 and 5). A printed circuit board 18 (FIG. 1) carries the electronic circuit for the photodiode 4a and is supported by means of carrier elements 19, 20 on casing part 8a. The fastening elements which can be used, such as screws and tapholes are not shown. By means of a connector 21a, 21b the printed circuit board 18 is electrically connected to a plug-in connection 22, which can receive a cable connection. In turn, the light emitting diode 3 is arranged on a printed circuit board 23, which is supported in grooves 24 or 25 of casing parts 8a or 9a (FIGS. 1, 2 and 7). The printed circuit board 23 also carries a plug-in connection 26, which can receive a cable connection.

As is apparent, on the one hand the six light emitting diodes 3 and on the other the six photodiodes 4a can be arranged in juxtaposed manner on the same casing 8a as the beam splitter 12 and in each case one light emitting diode 3 and one photodiode 4a is associated with each light channel 5a, whilst the beam splitter 12 is common to all six light channels 5a.

For testing the upper surface 11 of test material 1 by means of incident light, it is possible to directly use the described apparatus 10. In each test channel the photodiode 4a receives the portion of the light which is reflected or scattered back by the test material 1 and which passes from light emitting diode 3 via light channel 5a to test material 1, so that the latter is located in the light path between light source 3 and converter 4a. If the test material is transparent, it is possible to arrange below it (i.e. on the other side of the test material 1 compared with the apparatus 10) an optical element 20a, which for testing the complete layer thickness of test material 1 by means of back-scattered transmitted light can be a light absorber, or for testing the entire layer or the entire thickness of the spatial portion of the test material 1 by means of transmitted light a mirror. The optically essential elements of this arrangement are diagrammatically shown in FIG. 9, the optical element 28 being shown as a light absorber and the light beam is designated 3a.

In another variant of this construction the beam splitter element 12 is constructed as a strip mirror element, so that, as known from WO-87/03957, a streaked effect is obtained.

FIG. 1 shows below the test material 1 that part 29 of the inventive apparatus, which is associated with the testing of a layer or a spatial portion of the test material 1 by means of transmitted light. The second part 5b of the two-part light channel 5a, 5b is constructed as a parallelepipedic cavity 5b and passes through the second casing 6b.

At one end of the parallelepipedic cavity 5b is arranged a second optoelectronic converter 4b which, like the optoelectronic converter 4a, is an approximately quadrangular photodiode, whose photosensitive side is countersunk in a slot 30 (FIGS. 1, 4 and 8) provided for this purpose in the two casing parts 8b and 9b. A printed circuit board 31 (FIG. 1) carries the electronic circuit for the photodiode 4b and is supported by means of a carrier element 32 on casing part 8b, the fastening elements usable such as screws and tapholes not being shown. By means of a connector 33a, 33b the printed circuit board 31 is electrically connected to a plug-in connection 34, which can receive a cable connection.

At its other end the parallelepipedic cavity 5b terminates with the opening 5b visible in FIG. 6 opposite to the lower surface 35 of test material 1.

The apparatus according to the invention comprises two casings 6a, 6b and for each light channel the light emitting diode 3 is in the first casing 6a and the photodiode 4b in the second casing 6b in juxtaposed manner and arranged corresponding to a light channel. In the construction shown in FIG. 1 a part 5b of each light channel is arranged in the second casing 6b.

In each test channel the photodiode 4b receives the light portion transmitted by the test material 1 and this passes from the light emitting diode 3, via the light channel 5a to the test material 1 and from there via light channel 5b to photodiode 4b. Thus, the test material 1 is located in the light path between light source 3 and converter 4b. The optically essential elements of this arrangement are diagrammatically represented in FIG. 10.

In the hitherto described construction the test material 1 is substantially planar and the test material-side ends of the light channels 5a, 5b are congruent with a plane parallel to the test material 1. If the test material has a predetermined regular curvature, e.g. if it is constructed as a glass tube, the apparatus can be adapted to the shape of the test material, in that the test material-side ends of the light channels 5a, 5b are congruent with a surface, which is constructed and positioned parallel to the surface of the test material. In the case of a cylindrically or spherically curved test material then, in FIGS. 2, 3 and 7 the lower horizontal line of the drawing would be an arc instead of a straight line. In the case of a differently curved shape of the test material, the test material-side ends of the light channels 5a, 5b would be congruent with a surface correspondingly adapted to the test material surface, so as to be parallel thereto. The optically essential elements of such a construction are diagrammatically shown in FIG. 11, which will be described in detail hereinafter.

The walls of the light channels 5a, 5b are advantageously blackened, so as to be able to better define the light bundle of the light passing from the light source 3 to the test material 1 than if there were reflections on the walls of the cavities 5a, 5b. In a variant, the combination of light source 3 and light channels 5a, 5b can be constructed as a collimator, because a collimator is also an optical element defining the light bundle of the light passing from light source 3 to test material 1. The light sources 3 can also be constructed as laser diodes and in this case the construction of the light channels 5a, 5b and in particular the reflection characteristics of the walls thereof are not as critical, because the light bundle from the light diode is automatically well defined and the entity is an optical element defining the light bundle of the light passing from light source 3 to test material 1. In another variant the light channels can be constructed as Winston collectors and further variants of an optical element defining the light bundle of the light passing from the light source 3 to the test material 1 are conceivable.

In a further variant of the optical element, which defines the light bundle of the light passing from the light source 3 to the test material 1, as is diagrammatically shown in FIG. 11, the light source 3 is positioned remotely from the casing 6a and is connected to the light channel 5a via a light guide 36. The photodiodes 4b are also positioned remotely of casing 6b and are connected to the light channel 5b via a light guide 37. The same applies with regards to the photodiodes 4a in casing 6a, but this is not shown in order to simplify FIG. 11. The light guides 36 at the end thereof remote from light source 3 or photodiode 4a or 4b are inserted in the corresponding light channel over a certain length of light guide 36 or 37 and light channel 5a or 5b. In this sense, the light guides are at least partly arranged in at least part of a light channel.

FIG. 11 also diagrammatically shows that the inventive apparatus need only have a single light source common to all the test channels. In this variant all the light guides 36 are optically connected to said single light source 3 at the light source-side end thereof and said light source must naturally illuminate all the light guides 36 and is consequently advantageously a light emitting diode.

It is clear that the photodiodes 4a of FIG. 1 can also be connected with their associated light passages 16 via light guides, as is shown in the lower part of FIG. 11 with respect to photodiodes 4b and light channels 5b. The principle is the same and its use can be gathered in an obvious manner from FIG. 11, so that there is no need for a more detailed description.

FIG. 1 also shows that in the light channel 5a of the part 10 of the inventive apparatus located above test material 1 can be provided a further optical element 38, which is constructed as a plate in the same way as optical element 12 and is inserted in casing 6a by means of slots 39, 40 in much the same way as glass plate 12 by means of slots 13, 14. Slots 39 and 40 together form a recess for receiving the plate 38, when the casing parts 8a, 9a are joined together. Light passages 41, 42 are provided in the same way as light passages 15 and 16 and once again there is no need for light passage 41 if the wall of cavity 5a is constructed in such a light-absorbing manner that no undesired light from light emitting diode 3 and deflected by plate 38 returns to the latter and through it to the photodiode 4a.

In one construction of the optical element 38, the latter is in the form of a polarization filter or a colour filter. As in the case of optical element 12, the polarization or colour filters 38 associated with the individual test channels together form an individual subassembly, which is removably arranged in the casing. Such a polarization or colour filter permits a polarization or colour differentiated detection of the characteristics of the test material to be tested. The light passages 41 and 42 enable the light reflected on the polarization or colour filter 38 to pass out of the light channel 5a and to be optionally absorbed, so as to avoid a disturbance to the testing process by said light. As this takes place in much the same way as on light passage 15 with respect to optical element 12, it is not shown in order not to overburden the drawing. Here again, light passage 41 can be obviated, if the wall of the cavity 5a is given a corresponding light-absorbing construction.

In another construction of the optical element 38, the latter is constructed as a second beam splitter, which is once again in the form of a semitransmitting strip mirror forming a single subassembly and removably arranged in casing 6a.

In a first variant of this construction the photodiode 4c is arranged on casing 6a and on light passage 42 in much the same way as photodiode 4a on casing 6a and on light passage 16. The light reflected by beam splitter 38 reaches the photodiode 4c, in the same way as the light reflected by the beam splitter 12 in the case of photodiode 4a.

In a second variant of this construction the photodiode 4c is arranged on casing 6a, but now on light passage 41 in much the same way as photodiode 4a on casing 6a and on light passage 16. The light reflected by beam splitter 38 reaches the photodiode 4c, but it is now a portion of the light emanating from light source 3, so that the photodiode 4c is used for measuring and optionally regulating the light from light source 3.

It is equivalent to this second variant to leave the photodiode 4c, as in the first variant, on light passage 42 and to so symmetrically displace the beam splitter 38 with respect to interface 7a, that it deflects part of the light from light source 3 to photodiode 4c.

These different variants of an intrinsically unitary construction are mainly suitable for testing a surface of the test material by means of incident light or a layer or a spatial portion of the test material by means of back-scattered transmitted light.

In yet another construction of the optical elements 12 and 38, they are constituted by beam splitters, which are also constructed as strip mirror elements. They are constructed as parts of a semitransmitting strip mirror forming an individual subassembly and removably arranged in casing 6a. In each light channel the strips of the strip mirror elements are semitransmitting and essentially correspond to one another in the same way so that, as known from WO-87/03957, to bring about a streaked effect.

In general it is optically equivalent to move the construction formed by optical elements 12 and optionally 38 from casing 6a to casing 6b and it is also equivalent to intercharge light source 3 on casing 6a and photodiode 4b on casing 6b. For this arrangement the optically essential elements are diagrammatically shown in FIG. 12, an additional beam splitter 38' and its associated photodiode 4c' being provided on casing 6a in order to permit a measurement and optionally a regulation of the light from light source 3.

In the preceding description of the inventive apparatus and in the associated drawings, for simplification purposes, in each case a construction with juxtaposed test channels arranged in a single row has been chosen in exemplified manner. The walls between the light channels 5a or 5b are not shown in proportion to the other dimensions and are instead made much too thick. However, as the strength of the apparatus, due to the casing, is not dependent on said walls, they are in reality of the thinness to ensure that they are not transparent. Thus, a packing density of juxtaposed test channels is achieved, which permits an uninterrupted testing of the test material. However, it is better and in fact even necessary in the case of a stationary, flat test material in order to achieve an uninterrupted testing thereof to have two or more test channel rows in reciprocally displaced, juxtaposed manner with the necessary packing density. In the case of a construction with two reciprocally displaced rows of test channels this is diagrammatically shown by means of the second casing in FIG. 13, which is derived from FIG. 6. Elements 5b, 6b, 7b and 8b of FIG. 13 are the same as in FIG. 6. The equivalent of element 9b in FIG. 6 is now constructed in two-part form in FIG. 13, so that a second row of light channels 5b' can be arranged in the casing and namely parallel to the row of light channels 5b, but displaced with respect thereto, as shown in FIG. 13. Apart from the consequences of this displacement, casing part 9b' is equivalent to casing part 9b in FIG. 6. Between casing parts 8b and 9b' is provided a casing part 9b'', whose portion facing casing part 8b, with respect to the latter, fulfils the function of casing part 9b in FIG. 6, whilst its portion facing casing part 9b', with respect to the latter, fulfils the function of casing part 8b in FIG. 6, so that the interface 7b of FIG. 6 is replaced by two interfaces 7b' and 7b'' in FIG. 13.

The construction of the inventive apparatus remains essentially the same as that described hereinbefore in the case of an arrangement of several rows of test channels or light channels 5b and 5b', such as is e.g. shown in FIG. 13, i.e. the necessary adaptations are obvious to the Expert and there is no need to go into these here. For reasons of clarity, it is pointed out that optionally there are no light passages identical to light passages 15 and 41, if no space is available and their function is then fulfilled by a light-absorbing construction of the wall of the light channels. It is also pointed out that the light channels in FIG. 13 are shown with the same proportions as in FIG. 6. In fact it would be possible and even advantageous to choose the spacings between the light channels (i.e. the width of the walls separating them) the same as the width of said light channels, so that the areas of the test material which are detected by the light channels of the first and second row do not overlap and instead just join one another, so that the smallest possible and therefore most economic number of test channels is obtained for detecting a predetermined area of the test material.

If there are two rows of test channels or light channels, which are identical to one another, i.e. have the same number of test channels and are substantially parallel and closely juxtaposed, then one row can be associated with the light source-side part and the other row with the converter-side part of the inventive apparatus, so that both parts 10 and 29 thereof are located on the same side of the test material 1. The length of the light source-side part or the converter-side part of the light channel can be essentially reduced to zero and/or the wall between the light source-side part and the converter-side part of the light channel can in part be obviated, provided that the remaining part of the light channel adequately bounds the light passing from the light source to the test material.

The dimensions of the test channels need not be the same. It can be appropriate for various applications to enlarge the light channels e.g. from one end of the row to the other, or it can be appropriate to construct the light source-side part of the light channel with a different cross-sectional shape and/or cross-sectional surface to the converter-side part of the light channel. The light channels need not necessarily have the described quadrangular cross-sectional shape and the latter can e.g. be circular, whilst the corresponding cavity can be cylindrical or e.g. conical, pyramidal, etc.

The rows of test channels need not be linear and it can also be appropriate to arrange them along a curve, e.g. an arc for various applications.

I claim:

1. Apparatus for the simultaneous non-contacting testing of a surface or internal interface of a test material by means of incident light or a layer or spatial portion of the test material by means of back-scattered or back-reflected transmitted light, said apparatus comprising:
at least one light source for providing the incident light and said back-reflected transmitted light; and
a plurality of test channels, each test channel comprising an optoelectronic converter and at least one light channel arranged in the light path between said at least one light source and said optoelectronic converter, said at least one light channel having at least one beam splitter element arranged therein, said at least one light channel is constructed as an optical element for defining a light bundle on at least part of the light path located within the same, the light channels of said plurality of test channels, having a common plane of symmetry, are juxtaposed in a common casing and are constructed as recesses passing through said common casing, said common casing is constructed from first and second parts separable from one another in the common plane of symmetry, said at least one beam splitter element is constructed as part of a beam splitter forming a single subassembly and removably arranged in said casing, said optoelectronic converters are arranged on said casing and each correspond to one of said plurality of light channels, said test material is arranged in the light path between the light source and the optoelectronic converter.

2. Apparatus according to claim 1, characterized in that the test material side of the light channels are congruent with a surface constructed and arranged parallel to a surface of the test material.

3. Apparatus according to claim 1, characterized in that the at least one light source formed from light emitting diodes or laser diodes corresponding in each case to one light channel.

4. Apparatus according to claim 1, characterized in that the at least one light source positioned remotely of the casing and are connected to the light channels via light guides.

5. Apparatus according to claim 1, characterized in that the converters are formed from photodiodes corresponding to in each case one light channel, which are positioned remotely of the casing and are connected to the light channels via light guides.

6. Apparatus according to claim 4, characterized in that each light guide is at least partly arranged in at least part of a light channel.

7. Apparatus according to claim 1, characterized in that the two parts of the casing are provided with corresponding recesses, which form a recess for receiving the individual subassembly of the beam splitter on joining together the parts.

8. Apparatus according to claim 1, characterized in that at least one of polarization and color filter elements are located in the light channels and are constructed as parts of at least one of a polarization and a color filter forming a single subassembly and removably arranged in the casing.

9. Apparatus according to claim 8, characterized in that the two parts of the casing are provided with corresponding recesses, which form a recess for receiving the individual subassembly of the filter on joining together parts.

10. Apparatus according to claim 1, characterized in that the beam splitter elements are constructed as strip mirror elements.

11. Apparatus according to claim 10, characterized in that in each light channel is arranged a second strip mirror element, whose strips are semitransmitting and essentially correspond to the strips of the beam splitter element constructed as a strip mirror element, the second strip mirror elements being constructed as parts of a semitransmitting strip mirror removably arranged in the casing.

12. Apparatus according to claim 1, characterized by a second beam splitter element arranged in each light channel, the second beam splitter elements being constructed as parts of a beam splitter removably arranged in the casing and by in each case a second converter, which is positioned facing the second beam splitter element, in the same way as the first converter faces the first beam splitter element.

13. Use of the apparatus according to claim 1 for testing a supposedly smooth or regularly structured surface or internal interface of the test material for irregularities thereof.

14. Use of the apparatus according to claim 1 for testing a light transmitting, supposedly homogeneous or regularly structured layer or a light transmitting, supposedly homogeneous or regularly structured, spatial portion of the test material for irregularities therein including inhomogeneities and inclusions.

15. Use of the apparatus according to claim 1 for testing a supposedly stationary surface or internal interface of the test material for position changes to said surface, which are e.g. caused by movement, vibration, expansion, shrinkage, growth, deposits and the like.

16. Use of the apparatus according to claim 1 for testing the concentricity of a shaft for concentricity errors, particularly vibrations, as a function of the rotational speed of the shaft.

17. Use of the apparatus according to claim 1 for testing a light transmitting, supposedly stationary layer or a light transmitting, supposedly stationary spatial portion of the test material for movements and in particular vibrations of inhomogeneities and inclusions in the test material, as well as particles suspended or floating therein.

18. Use of the apparatus according to claim 13, characterized in that on one side of the test material is located the apparatus for testing the test material by means of incident light or back-scattered transmitted light and on the other side thereof is provided a retroreflector for the transmitted light.

19. Use according to claim 13, characterized in that on one side of the test material is provided the apparatus for testing the test material by means of incident light or back-scattered transmitted light and on the other side of the test material is positioned an absorber for the transmitted light.

20. Use according to claim 15, characterized in that on one side of the test material is provided the apparatus for testing the test material by means of incident light or back-scattered transmitted light and on the other side of the test material is provided a retroreflector for the transmitted light.

21. Use according to claim 15, characterized in that on one side of the test material is provided the apparatus for testing the test material by means of incident light or back-scattered transmitted light and on the other side of the test material is provided an absorber for the transmitted light.

* * * * *